United States Patent [19]

Osanai

[11] 4,432,374

[45] Feb. 21, 1984

[54] PLETHYSMOGRAPHIC ACCELERATION PULSE WAVE METER

[76] Inventor: Hiroshi Osanai, Miyamaedaira Green Heights 17-403, Mukogaoka 430, Takatsu-ku, Kawasaki-shi, Kanagawa-ken, Japan

[21] Appl. No.: 325,012

[22] Filed: Nov. 25, 1981

[51] Int. Cl.$^3$ .............................................. A61B 5/02
[52] U.S. Cl. ..................................... 128/694; 128/666
[58] Field of Search ....................... 128/672, 687–690, 128/666, 691–694, 713, 714

[56] References Cited

U.S. PATENT DOCUMENTS

| | | | |
|---|---|---|---|
| 3,881,481 | 5/1975 | Heule et al. | 128/666 |
| 3,920,004 | 11/1975 | Nakayama | 128/691 X |
| 4,105,021 | 8/1978 | Williams et al. | 128/683 |
| 4,137,910 | 2/1979 | Murphy | 128/713 |
| 4,154,238 | 5/1979 | Link | 128/681 |
| 4,301,809 | 11/1981 | Pinchak | 128/715 X |

OTHER PUBLICATIONS

Devi, V. L. et al., "A Processing System for Automatic On-Line Determination of LVET", Changes in Health Care Instrumentation Due to UP Technology, Conf: Proc. of the IFIP-IMIA Rome, Italy (Feb. 6–8, 1980) pp. 167–173.

Primary Examiner—Kyle L. Howell
Assistant Examiner—Francis J. Jaworski
Attorney, Agent, or Firm—Jordan B. Bierman; Linda Bierman; C. Cornell Remsen, Jr.

[57] ABSTRACT

A plethysmograph is provided with a sensor for detecting an increase or decrease in the blood volume of a vascular bed, preferably by photoelectrically detecting blood content in a finger-apex position. The detection signals derived from the sensor are twice or triply differentiated to produce an acceleration curve indicative of blood circulation whose interpretation effectively leads to a diagnosis of the entire circulatory system including early signs of malfunction. Detection of the presymptoms of arteriosclerosis, myocardial infarction, cerebral apoplexy, subarachnoidal hemorrhage, etc. is possible and the apparatus may be used to monitor the patient's condition during subsequent treatment. A visual or printed card of the diagnostic results can be provided.

6 Claims, 65 Drawing Figures

PLETHYSMOGRAPHIC ACCELERATION PULSE WAVE METER

BACKGROUND OF THE INVENTION

1. Field of the Invention

The present invention relates to an acceleration plethysmograph, which can detect acceleration of a change in the contained-blood volume of a finger-apex, which is greatest in contained-blood volume and easily detected.

2. Description of the Prior Art

In the past, the functional examination of circulatory organs has been relied upon an electrocardiogram and blood pressure. However, apart from the blood pressure, opinion is divided on the electrocardiogram in interpretation thereof and problems are involved, which is therefore difficult to understand. Also, the electrocardiogram, for example, such as an exercise electrocardiogram, can detect a change in function in a special case, and a given organic change possibly appears, but it cannot judge the quality of circulation to assist in the prevention of future disease and to provide data necessary to recover the function.

Recent cases indicate that a person who does not always suffer high blood pressure is very often subject to infarction or subarachnoidal hemorrhage, and the mutual relationship therebetween is unkown, and accordingly, there is a demand of a new examination means.

On the other hand, a plethysmograph has been used as one of examination means of the circulatory function. That is, the pulse wave indicative of an increase or decrease in volume of blood within a capillary blood vessel is mechanically or electrically obtained as a fluctuation. A sensor for a plethysmograph measures a change in physical volume of fingers or the like, a change in impedance and a change in light permeability. The parts used for detection may include not only peripheral organs but various parts of the body. Clinically speaking, the peripheral blood stream is checked to thereby use it for examination of an abnormality of the aortic valve, the degree of arteriosclerosis, propagation time, the effect of a blood vessel expanding agent, the adjustment of vascular exercise, the indication of toxic symptoms resulting from the presence of poisonous matter within the body of a woman during pregnancy. This known method however is unreliable because it can be affected by temperature, tension of mind, drugs, respiration, etc. and in addition, a delusion in judgement may occur due to the obscurity of shape of the plethysmogram. For this reason, other examinations had to be referred to while reserving judgement resulting from said method. This method therefore is rarely utilized in plethysmography these days, and a plethysmograph is merely used as a heart beat signal of a heart beat meter.

SUMMARY OF THE INVENTION

It is therefore an object of the present invention to provide an apparatus in which the characteristics of individual persons to be examined can be obtained from the information of a plethysmograph to thereby easily extract information which is highly related to the clinical results of circulatory dysfunction.

In the embodiments of the plethymograph according to the present invention, a finger-apex is selected as the art to be examined for the reasons as follows:

The pulse wave in the finger-apex serves as the observing means at a location where a blood capillary is mostly developed and a content of blood is large, in measuring the movement of blood from a peripheral artery to a vein, and therefore the finger-apex can be said take the optimum point in measuring the condition of circulation. Locations relatively easily available having the greatest number of blood capillaries are a finger-apex and an ear-lobe. Generally, however, it is considered that the contained-blood volume is present more in the finger-apex so that a change thereof may be easily measured. If an impedance pulse wave is used instead of the photoelectric pulse wave, it is possible to obtain the pulse wave even from vascular beds other than the finger-apex. However, waveforms involving a considerable number of primary factors may be seen in view of the construction of the blood vessel system, and it is difficult to analyze the meaning of such waveforms.

In addition, the finger-apex is always exposed and is accessible to the detection portion of the examination apparatus, which construction may be advantageously designed simply.

Incidentally, causes influencing on the pulse wave of the finger-apex include three points as follows:

(1) From the artery side
  a. Heart beat
  b. Distribution of blood to the upper limbs
  c. Elasticity of artery system
  In a, b and c, it functions as the continuous force.
(2) From the blood capillaries
  Content of blood determined by density and diameter, Temperature
(3) From the vein side
  a. Diastole
  b. Elasticity of vein
  c. Pressure functions as negative pressure Since the pulse wave of finger-apex measures a change in contained-blood volume, blood extruded by the heart beat arrives at the blood capillaries after a delay of a given time. Since the blood is present also in the vein side, the blood does not flow uniformly through the blood capillaries to the vein but remains in the artery side by a portion in excess of the range of blood received by the vein. However, extrusion pressure on the artery side is well above the volume of blood moving to the vein, the cycle which reduces as the blood capillaries of the finger-apex expand is repeated. This transition is measured by the pulse wave of the finger-apex. However, relatively continuous pressure is applied to the artery system due to the heart beat, elasticity of the artery system or the like whereas in the vein system, the vein wall is relatively thin and the elasticity is less, and in addition is subject to the influence thereon by the diastole, as a consequence of which a change in pressure is delicate. Accordingly, the waveform of the pulse wave of the finger-apex is varied while being affected by the delicate change in pressure of the vein system. The change in content of blood can be known from the ordinary pulse wave, and the speed of increase or decrease in content of blood can be seen by the waveform through a linear differentiation. However, information on the change in content of blood corresponding to the change in pressure of the vein system cannot be well determined unless it is differentiated once again into an acceleration curve.

Considering now the quadratic differentiation of the volume of blood V contained in the blood capillaries as a model, V may be written as the product of a sectional area S in vessel of a blood-contained portion and the length of said contained portion as in the following equation:

$$V = l \cdot S \qquad (1)$$

Differentiating V, l, S as the fluent at time t, then $$\frac{dV}{dt} = l \cdot \frac{dS}{dt} + \frac{dl}{dt} \cdot S \qquad (2)$$

Further differentiating them once again at time t, then $$\frac{d^2V}{dt^2} = \frac{dl}{dt} \cdot \frac{dS}{dt} + l \cdot \frac{d^2S}{dt^2} + \frac{d^2l}{dt^2} \cdot S \frac{d}{dt} \cdot \frac{dS}{dt} \qquad (3)$$

$$= 2 \cdot \frac{dl}{dt} \cdot \frac{dS}{dt} + l \cdot \frac{d^2S}{dt^2} + \frac{d^2l}{dt^2} \cdot S$$

In the right side, the first term represents the product of the flow speed of blood and the expansion speed of the blood capillary, the second term represents the product of the content of blood and the expansion speed of the blood capillaries, and the third term represents the product of the blood flow acceleration and the sectional area of the blood contained portion. It is here considered that the flow speed and flow acceleration are affected by pressure of residual blood on the peripheral vein side, and the expansion speed of the sectional area and the expansion acceleration are affected by the residual blood in the peripheral vein and the expansion resistance of the blood capillaries.

The quadratic differentiated figure illustrates the change in acceleration of the content of blood in the capillary vessel. In other words, it illustrates a change in speed produced in response to a delicate change in vein pressure. In the past, the delicate change in vein pressure has not been determined by the peripheral vein, and also, the quadratic differentiated figure of the pulse wave has not been accounted for sufficiently. However, it seems that the waveform has a given pattern and the recognition of this pattern can provide data by which the quality of the blood circulation may be judged with considerable accuracy.

Figure 2:
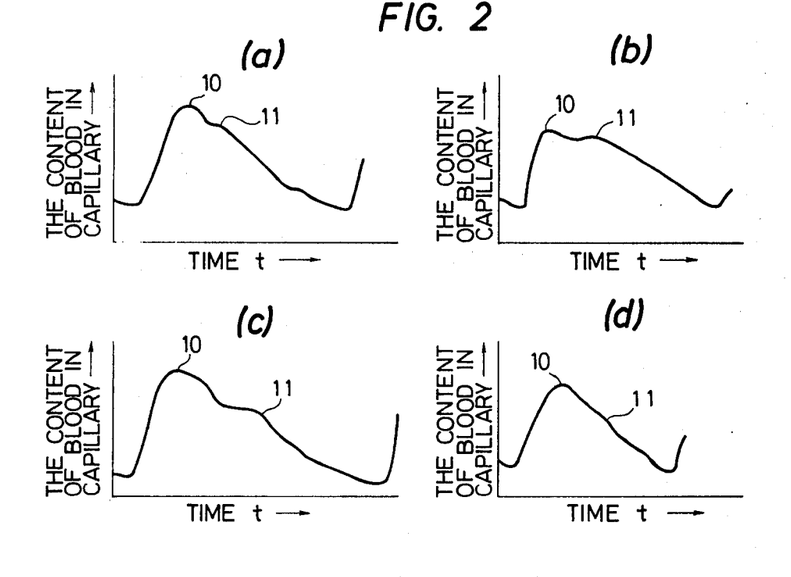
FIG. 2 (a, b, c and d) shows pulse waves of blood contact in a capillary.
Figure 3:
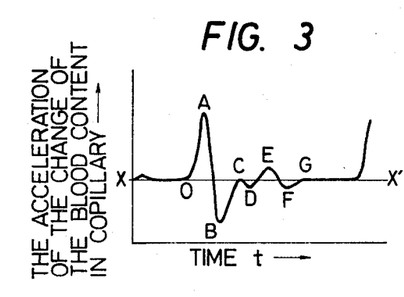
FIG. 3 is a quadratic differentiated figure (acceleration pulse wave curve) in accordance with the present invention.
Figure 4:
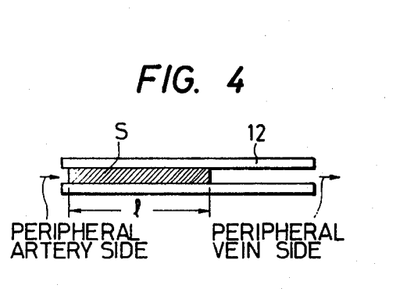
FIG. 4 is a schematic view illustrating blood flow in blood capillaries.
Figure 5:
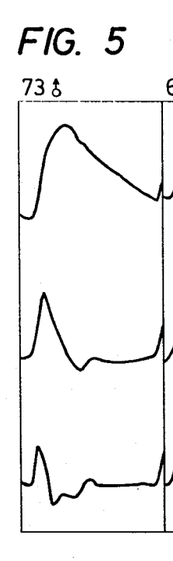
FIGS. 5, 6, 7, 8, 9, 10, 11, 12, 13, 14 and 15 are respectively views showing pulse waves, changed speed thereof, and changed acceleration thereof for eleven persons examined.
Figure 6:
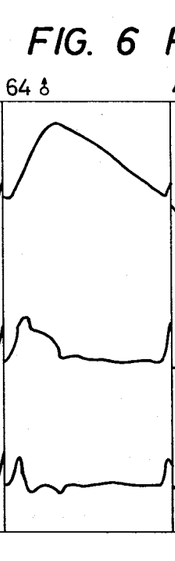
Figures 7, 8:
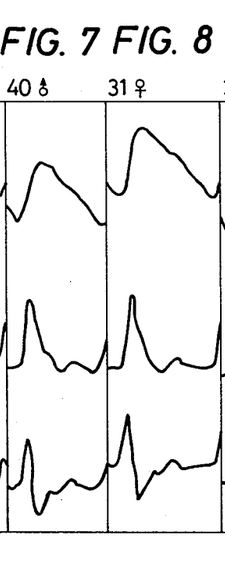
Figures 9, 10, 11:
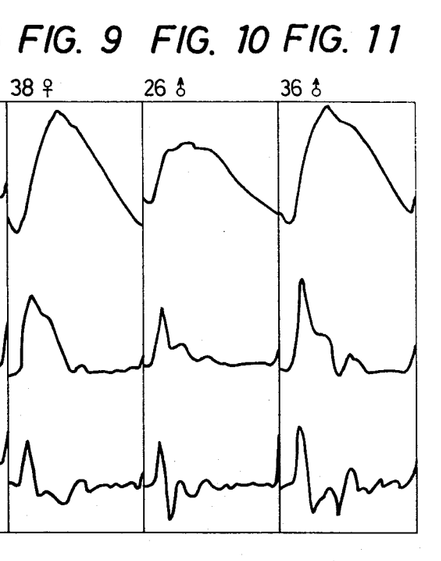
Figure 12:
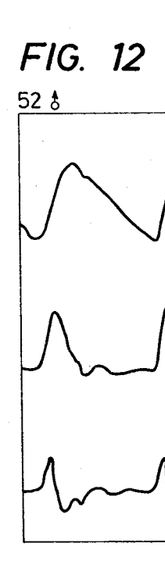
Figure 13:
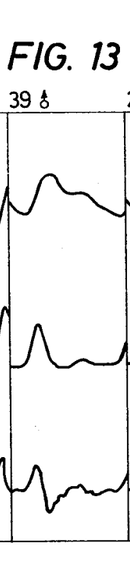
Figure 14:
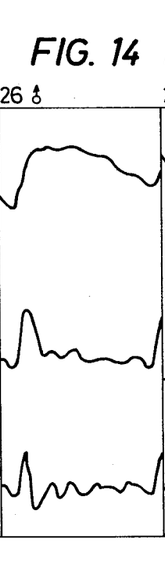
Figures 15, 16:
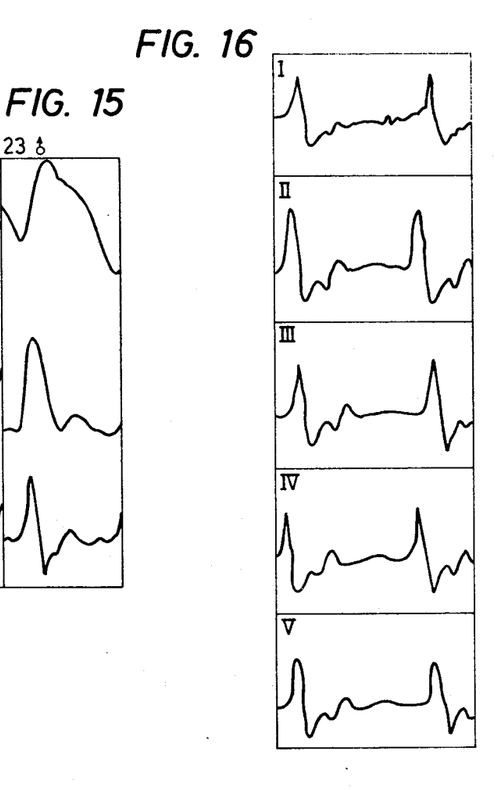
FIG. 16 is a comparative view for the presence of a difference in the acceleration pulse wave curve by way of fingers.
Figures 17, 18:
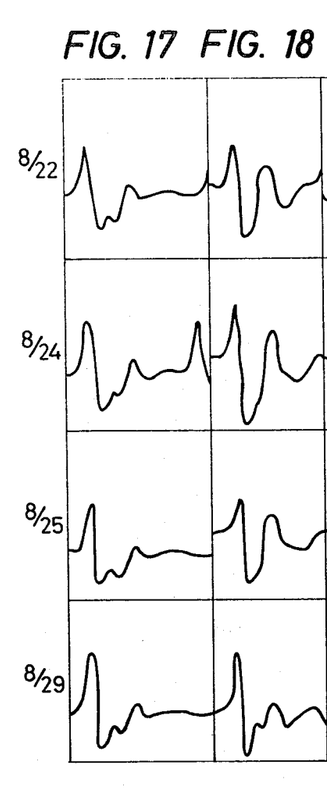
FIGS. 17, 18, 19, 20, 21, 22, 23, 24, 25, 26, 27, 28, 29, 30, 31, 32, 33, 34, 35, 36, 37, 38, 39, 40, 41, 42, and 43 are respectively views showing changes in acceleration pulse wave curve when exercise is imposed on 27 persons examined.
Figure 19:
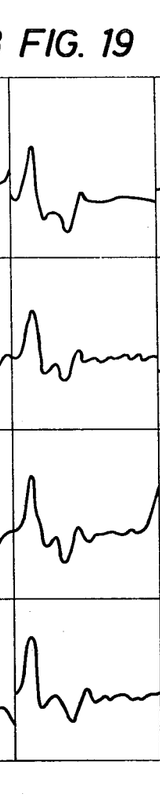
Figure 20:
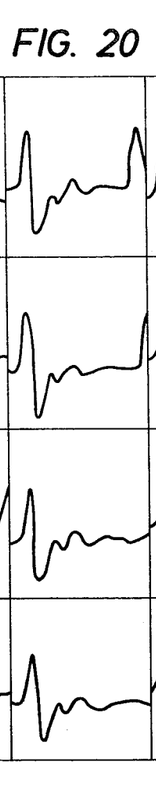
Figure 21:
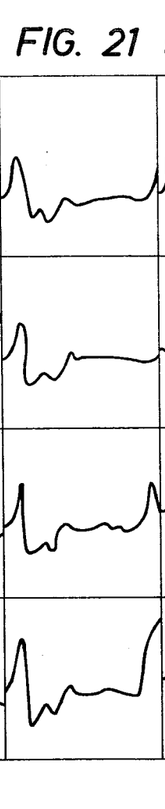
Figure 22:
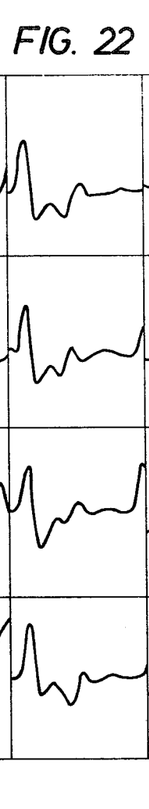
Figure 23:
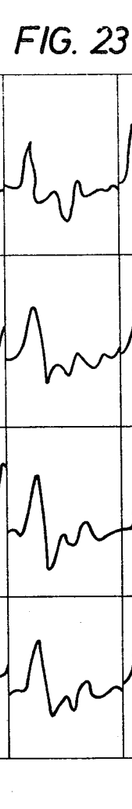
Figure 24:
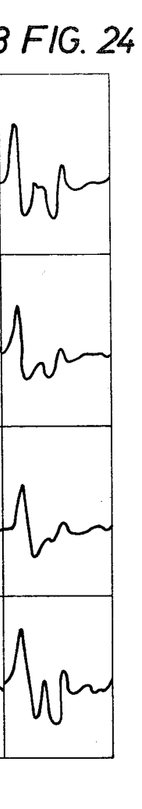
Figure 25:
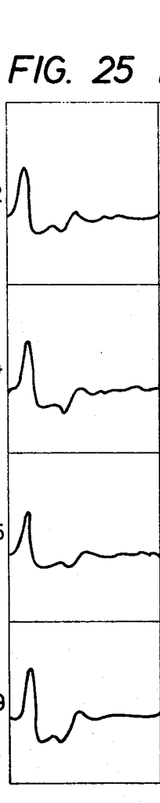
Figure 26:
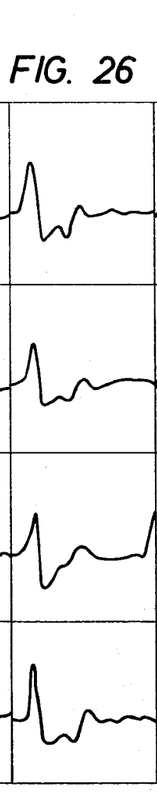
Figure 27:
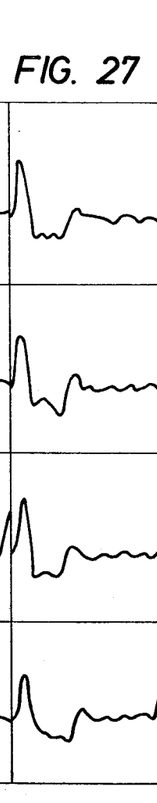
Figure 28:
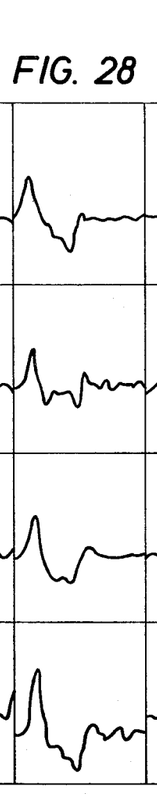
Figure 29:
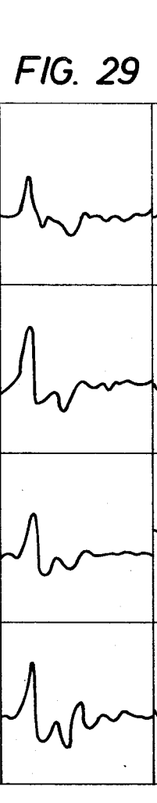
Figure 30:
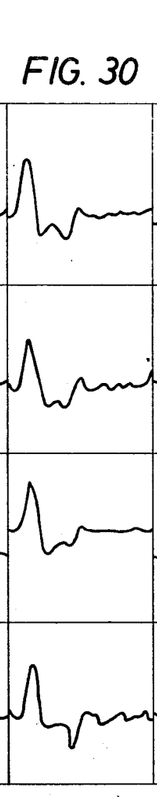
Figure 31:
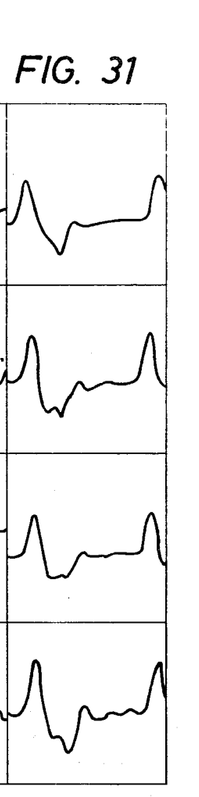
Figure 32:
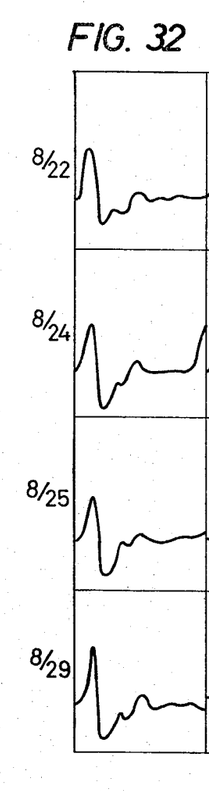
Figure 33:
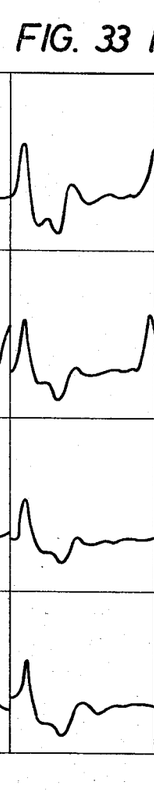
Figures 34, 35, 36:
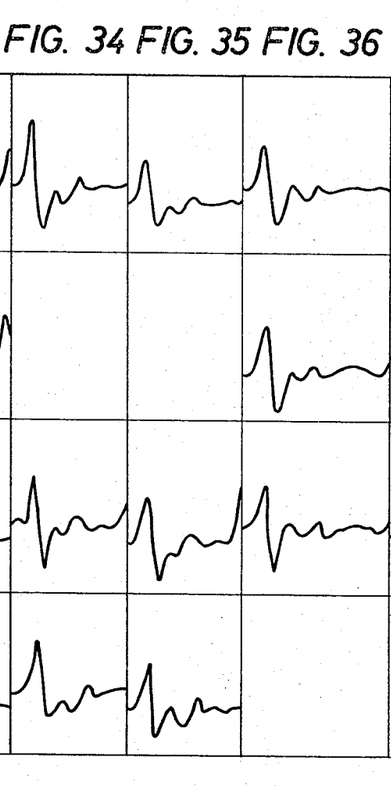
Figure 37:
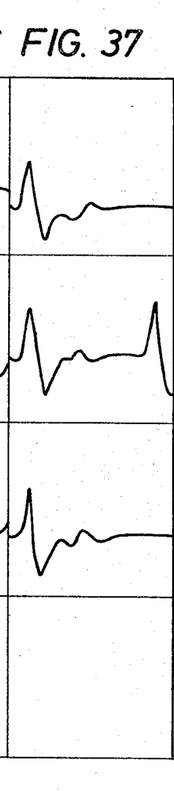
Figure 38:
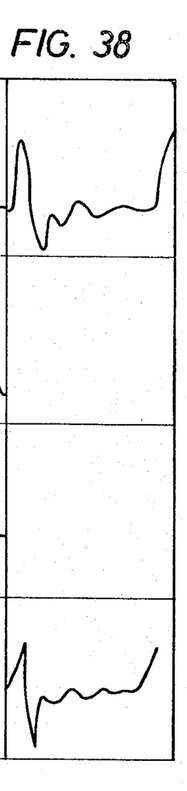
Figures 39, 40:
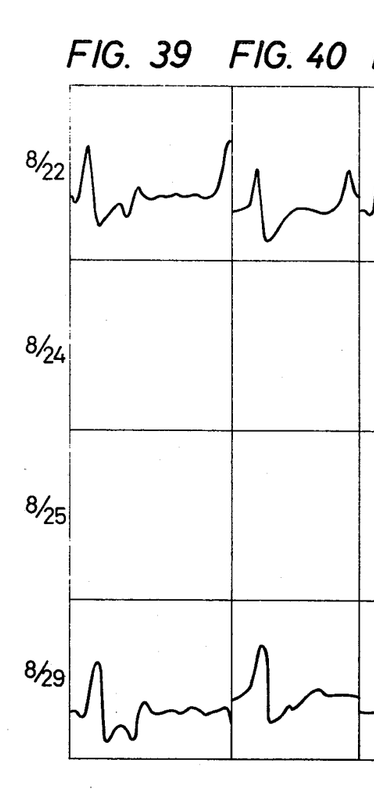
Figures 41, 42:
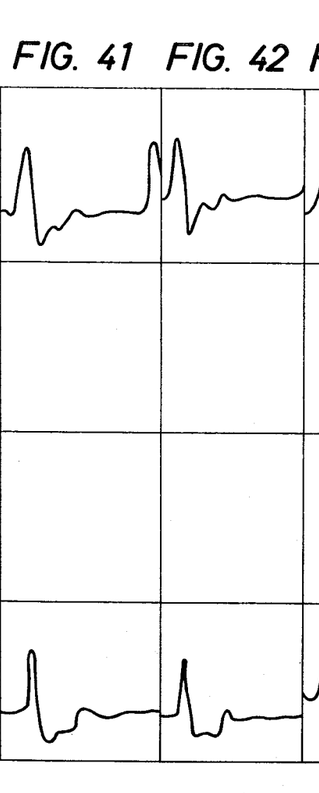
Figure 43:
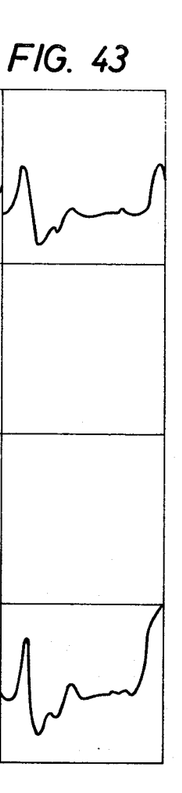

Referring now to the quadratic differentiated figure of the pulse wave shown in FIG. 3, when heart beat blood having a blood pressure of 20–30 mmHg arrives at a small artery and flows into the blood capillaries, the volume of said blood is in excess of that delivered towards the vein through the capillary vessel and as a consequence, the change in acceleration of the content in the capillary vessel rapidly increases (O→A). Such an increase is rapidly reduced subsequently, since the blood in the capillary vessel is fed to the vein (A→B), and in the case that the vein is filled with blood to some extent, the blood from the vein stays in the capillary vessel once again with the result that the acceleration of the change in contained blood volume in the capillary vessel tends to increase (B→C). For the same reason as mentioned previously, fluctuation is repeated in which the acceleration then is reduced slightly (C→D), further increases (D→E) and then reduces (E→F), after which point G, the change remains inconsequential. This can be seen also in the waveform shown in FIG. 2 which is normally measured as a pulse wave, but it has been heretofore merely used as a minute point of inflection and thus analysis has been difficult.

In accordance with the present invention, movement of blood from the artery to the vein through the blood capillaries is not measured as a given flow but measured as a fluctuation corresponding to the change in mutual pressure to read data for judging of the quality of the blood stream from the shape of the fluctuation, thereby definitely extracting the characteristics thereof.

DESCRIPTION OF THE PREFERRED EMBODIMENTS

The construction of a plethysmograph in accordance with the present invention will now be described in detail by way of one embodiment.

Embodiment 1

Figure 1:
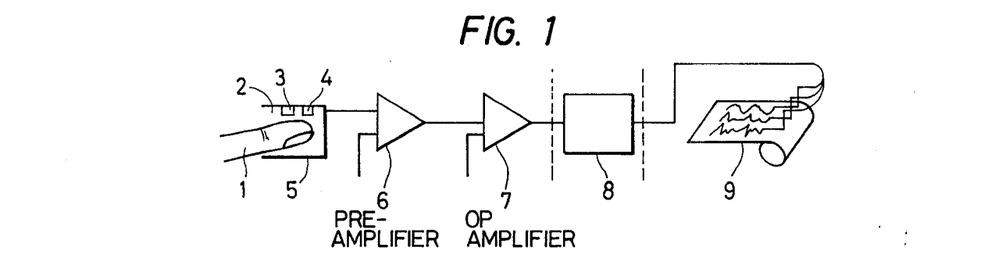
FIG. 1 is a block diagram of an acceleration plethysmograph according to the present invention.

As shown in a block diagram of FIG. 1, the plethysmograph comprises a finger-apex pulse wave pick-up 5 provided with an opening 2 into which a finger 1 is inserted, a light source 3 and a photoelectric element 4, a preamplifier 6, an OP (operational amplifier) 7, a characteristic extraction circuit 8 and a pen-written oscillograph 9. In the embodiment shown in FIG. 1, three kinds of graphs, i.e., a pulse wave, a once-differentiated value of the pulse wave and a twice-differentiated value thereof, but the function of the characteristic extract circuit 8 is not limited thereto as will be described later. In such an apparatus as described above, pulse wave waveforms and varying acceleration waveforms in which said pulse waveforms are differentiated twice continuously for time t by the characteristic extract circuit 8 were observed with the result that waveforms as in FIG. 2 (a, b, c, d) and FIG. 3 were obtained. For carrying out a quadratic differentiation, two stages of an analog differentiating circuit (not shown) employing a CR capacitor/resistor circuit were employed. The axis of the abscissa indicates the time t, and the axis of the ordinate indicates the volume of blood contained in a capillary vessel (hereinafter referred to as "the contained-blood volume" and the varying acceleration of the same.

In FIG. 2(a), the peak 10 is constantly delayed in time corresponding to the heart beat whereas the peak 11 subsequently appeared is considered to correspond to the contained-blood volume on the vein side. There are cases such as being sharply recognizable as in FIG. 2 (b), recognizable at a point where the contained-blood volume decreases as in FIG. 2 (c), dimly recognizable slightly delayed from the peak 10 as in FIG. 2 (a), and hardly recognizable as in FIG. 2 (d), which cases are not constant, resulting in making a painstaking judgment thereof, which leads to the result that the pulse wave curve is of no practical value, as previously described.

Observing now waveforms (FIG. 3) of the varying acceleration of the contained-blood volume of the blood capillaries in accordance with the present invention, there is normally recognized three peaks (A, C, E) and two valleys (B, D) therebetween, and as compared with a number of clinical examples, the state of blood movement from artery to vein through the blood capillaries can be distinguishably known from the height of peak C and depth of valley D relative to the refference line X-X'. It is observed that the peak C is high and the valley D is shallow for a young and high-spirited person who is in the good condition of blood circulation. And, for a middle and advanced aged person who is poor in circulation of the blood, sometimes the peak C does not only reach the reference line but is hardly recognized and such a change can be recognized in that the valley D becomes extremely deepened much more than the valley B. It has become obvious that information representative of such poor circulation of the blood is obtained.

The difference between the above-mentioned coventional pulse wave and the acceleration pulse wave obtained by the plethysmograph in accordance with the present invention will be explained with reference to actual examples shown in FIGS. 5, 6, 7, 8, 9, 10, 11, 12, 13, 14 and 15. These figures respectively show the measured results obtained from the age of 73 male, 64 male, 40 male, 31 female, 38 female, 26 male, 36 male, 52 male, 39 male, 26 male, and 23 male in order from FIG. 5, the upper column being representative of the conventional pulse wave, the middle column the curve differentiated at time t, and the lower column the quadrative differentiated figure further differentiated once again at time t. It is hardly possible to discuss the difference between individuals from the pulse wave in the upper column and is difficult to clarify the difference even from the waveforms in the middle column. The quadrative differentiated figure in the lower column is the curve having a given pattern divided into several peaks and valleys different from the waveforms in the upper and lower columns and it is possible to say something or other of the individual difference with respect to the relative height of peak and relative depth of valley.

These curves in the upper, middle and lower columns are concerned with a transition of the content of blood in the blood capillaries. The upper column indicates the transition by time of the content of blood in the blood capillaries in response to movement of heart beat, the middle column indicates the transition of speed of increase or decrease in the content of blood, and the lower column indicates the speed or acceleration in change of said speed. These curves all indicate the relative movement, but the difference depending on individuals and ages is most plainly indicated by the acceleration pulse wave curve in the lower column.

In case of one and the same person, there is not recognized a difference by fingers. That is, in FIG. 16 (I, II, III, IV, V), the quadrative differentiated figures were compared between fingers from the first finger to the fifth finger, and as a result, only the first finger showed unifitness as a sensor, and the second to fifth fingers mostly showed the same pattern. It is to be understood that unless the finger-apex gets excessively cold so as to minimize the circulation of blood, in the case of the one and the same person, a pattern peculiar to said person is represented irrespective of diameter of the finger.

Since the acceleration pulse wave curve is a reflex of the state of a blood flow in the capillary vessel, it also shows a form peculiar to an individual. For example, it is considered that if one takes a run for a long period of time, he can maintain his good blood flow condition for a long period of time, and if one engages in continuous training, he can maintain his good blood flow condition. Loads or excercises such as various preparatory gymnastics, and runnings are imposed on an examined group given in Tables 1-1 and 1-2 to observe a change of the acceleration pulse wave curve in their rest conditions, which examples are illustrated in FIGS. 17, 18, 19, 20, 21, 22, 23, 24, 25, 26, 27, 28, 29, 30, 31, 32, 33, 34, 35, 36, 37, 38, 39, 40, 41, 42 and 43.

TABLE 1-1

| | FIG. | | | | | | | | | | | | |
|---|---|---|---|---|---|---|---|---|---|---|---|---|---|
| | 17 | 18 | 19 | 20 | 21 | 22 | 23 | 24 | 25 | 26 | 27 | 28 | 29 |
| Sex distinction ♂ | O | O | O | | | | | | | | | | |
| Sex distinction ♀ | | | | O | O | O | O | O | O | O | O | O | O |
| Age | 46 | 47 | 60 | 34 | 60 | 39 | 41 | 51 | 52 | 53 | 53 | 54 | 53 |
| Blood pressure | 152/102 | 145/111 | 167/94 | 113/70 | 133/70 | 161/108 | 145/101 | 179/117 | 107/69 | 149/95 | 149/79 | 115/74 | 126/79 |
| Rest pulse/min. | 77 | 101 | 69 | 78 | 67 | 67 | 77 | 72 | 59 | 66 | 63 | 59 | 63 |
| '80.8.22 Measurement | O/ | O/ | O/ | O/ | O/ | O/ | O/ | O/ | O/ | O/ | O/ | O/ | O/ |
| Load | | | | | | | | | | | | | |
| '80.8.24 Measurement | O | O | O | O | O | O | O | O | O | O | O | O | O |
| Load | 1 | 10' X 2 | 10' | 1 | 10' X 2 | 60' | 1 | 40' | 2 / 3 | 30' | 10' X 3 | / | 2 / 3 |
| '80.8.25 Measurement | O | O | O | O | O | O | O | O | O | O | O | O | O |
| Load | 120' | 30' | 10' | 1 | 25' | 4 / 5 | 60' | 1 | 1 / 3 | 1 | 20' | 10' X 2 | 2 / 3 |
| '80.8.29 Measurement | O/ | O/ | O/ | O/ | O/ | O/ | O/ | O/ | O/ | O/ | O/ | O/ | O/ |
| Load | | | | | | | | | | | | | |

TABLE 1-2

| | FIG. | | | | | | | | | | | | |
|---|---|---|---|---|---|---|---|---|---|---|---|---|---|
| | 30 | 31 | 32 | 33 | 34 | 35 | 36 | 37 | 38 | 39 | 40 | 41 | 42 | 43 |
| Sex distinction ♂ | | | | | | | O | O | O | | | | | |
| Sex distinction ♀ | O | O | O | O | O | O | | | | O | O | O | O | O |
| Age | 59 | 57 | 60 | 52 | 39 | 53 | 30 | 40 | 33 | 39 | 49 | 52 | 54 | 54 |
| Blood pressure | 134/90 | 99/78 | 115/76 | 140/81 | 166/93 | 150/91 | 97/72 | 115/72 | 104/70 | 140/88 | 164/68 | 139/76 | 139/74 | 122/80 |
| Rest pulse/min. | 65 | 69 | 73 | 74 | 85 | 81 | 60 | 55 | 69 | 68 | 107 | 75 | 78 | 73 |
| '80.8.22 Measurement | O/ | O/ | O/ | O/ | O/ | O/ | O/ | O/ | O/ | O/ | O/ | O/ | O/ | O/ |
| Load | | | | | | | | | | | | | | |
| '80.8.24 Measurement | O | O | O | / | / | O | O | / | / | O | / | O | / | / |
| Load | / | 10' X 3 | 2 / 3 | 20' | 25' | 10' X 2 | / | / | 1 | 10' X 3 | 40' | 10' X 3 | 25' | 25' |
| '80.8.25 Measurement | O | O | O | O | O | O | O | O | / | / | / | / | / | / |
| Load | 1 | 25' | 2 / 3 | 25' | 1 | 1 | / | / | / | / | 2 / 3 | 25' | 20' | 25' |
| '80.8.29 Measurement | O/ | O/ | O/ | O/ | O/ | O/ | / | / | O/ | O/ | O/ | O/ | O/ | O/ |
| Load | | | | | | | | | | | | | | |

In the Tables, loads 1, 4/5, 2/3, and 1/3 are abridgements of one circuit of Lake Yamanaka, 4/5 round, 2/3 circuit and 1/3 circuit, respectively. Others indicate the running time and frequencies.

Figure 44:
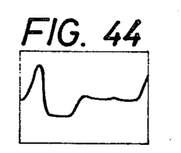
FIGS. 44, 45, 46 (a) (b) and 47 are respectively views showing the acceleration pulse wave curve of persons having past anamnesis, i.e., the hindrance of circulation indicating possible myocardial infarction, cerebral apoplexy, etc.
Figure 45:
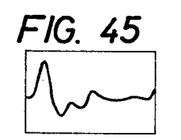
Figure 46:
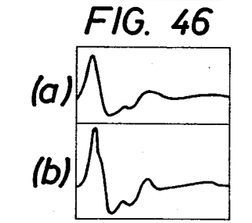
Figure 47:
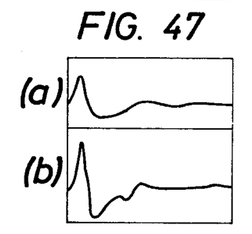

These cases vary according to the age, sex distinction, volume and time of training or running, conditions of daily life and so on, but some show a change, return to their original conditions or further improvement. The acceleration pulse wave curves for four persons with other anamnesis are illustrated in FIGS. 44, 45, 46 (a) (b), and 47 (a) (b). In FIG. 44, in the case of a certain person of age 50, 1973: angina pectoris, 1975: myocardial infarction, 1979: start of training, August 1979: discovery of myoma uteri, November 1979: operation on the same, June 6, 1980: measurement of acceleration pulse wave (FIG. 44), and thereafter loss of contact with her, probably died. In FIG. 45, in the case of a further certain person of age 45, May 1977: operation of myoma uteri, April 1980: start of training, Apr. 4, 1980: measurement of acceleration pulse wave (FIG. 45), the trend of improvement as compared with the case of FIG. 44 is apparent. In FIG. 46, in case of a certain person of age 56, April 1960: angina pectoris, April 1976: start of training, Apr. 4, 1980: measurement of acceleration pulse wave (FIG. 46 (a)). July 1, 1980: measurement of acceleration pulse wave (FIG. 46 (b)), the trend of improvement is not recognizable between as the two figures, remaining on the same level; thereafter there was loss of contact with her. She was probably dead. In FIG. 47, in case of a certain person of age 58, 1969: subarachnoidal hemorrhage, September 1976: start of training, Apr. 4, 1980: measurement of acceleration pulse wave (FIG. 47 (a)). June 6, 1980: measurement of acceleration pulse wave (FIG. 47 (b)), the trend of improvement is recognizable as between the two figures, and one was assured from other diagnostic results that she is on the road of recovery.

Next, how to read the acceleration pulse wave curve will be described.

Pattern analysis of acceleration pulse wave curve (I)

Figure 48:
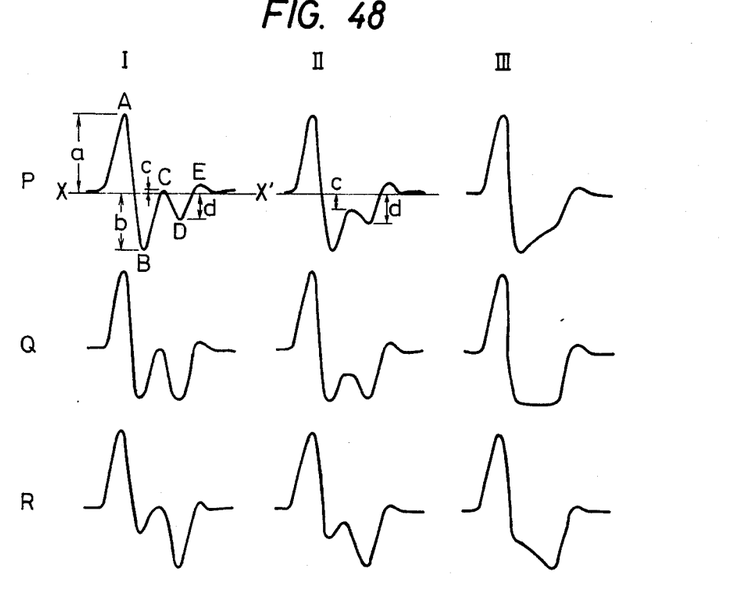
FIG. 48 is a classification pattern of the acceleration pulse wave curve.

The quadrative differentiated figure of the pulse wave usually illustrates the peaks and valleys at A, B, C, D and E as shown in FIG. 48, from various cases so far discussed. The degree of the depth of valley B and valley D, can be divided into three relationships, i.e., b>d, b≈d, and b<a, and there also can be roughly divided into three, the point that the height of the peak C is higher or lower than the reference line X-X'.

The pattern in P-I is recognized in a young and high-spirited person who is good in circulation of the blood, and the pattern in P-II is recognized in a young person but often in a middle and advanced aged person who is relatively high-spirited.

The pattern in P-III is recognized in a person having tachycardia.

The pattern in Q-I–III indicates a person who has a somewhat high blood pressure, and is a pattern which shows that the contained-blood volume of the vein increases slightly with the result that the circulation of blood tends to be somewhat poor.

A person representative of the pattern is R-I–III often has high blood pressure, and this pattern is considered to be a pattern representative of a poor blood flow in the capillary vessels resulting from an increase in pressure of the veins.

However, from experience these patterns are not always related to blood pressure at that time, but represent the quality of circulation of the blood. At the least types Q and R require care and if such conditions continue, a dangerous hindrance of circulation may result, in which case, an improvement through training, running and so on is desirable.

Pattern analysis of acceleration pulse wave curve (II)

Figure 49:
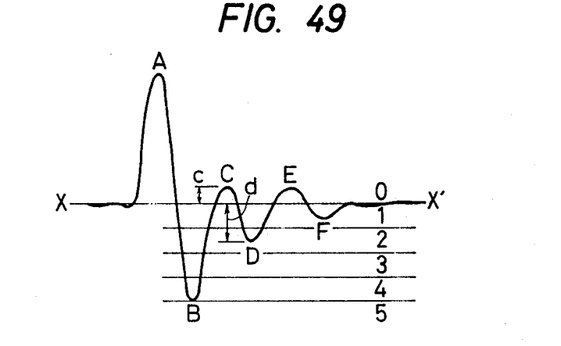
FIG. 49 is a conceptual curve for counting the marks relating to the blood flow of individuals from a single quadratic differentiated figure.

As shown in FIG. 49, the acceleration pulse wave curve has the peaks and valleys at A, B, C, D, E, and F, among which is featured by the height c of point C relative to the reference line X-X' and the depth d of point D relative to the reference line X-X'. For example, in FIG. 50 (a), an advanced aged group over 60 years old was selected as the examined persons from participants in a training and swimming class-room in Tama Sports Clubhouse and those in Hachioji Athletic Clubhouse. These 121 persons were examined to show how many person score the point C by age, provided that the depth b from the reference line to point B is divided into four parts so that 0 point is given for those above the reference line, one point for those directly below the reference line, and two, three, four and five points for those therebelow. As the age advances, there are many persons who have higher marks, and the average marks by the age tends to gradually increase.

Figure 50:
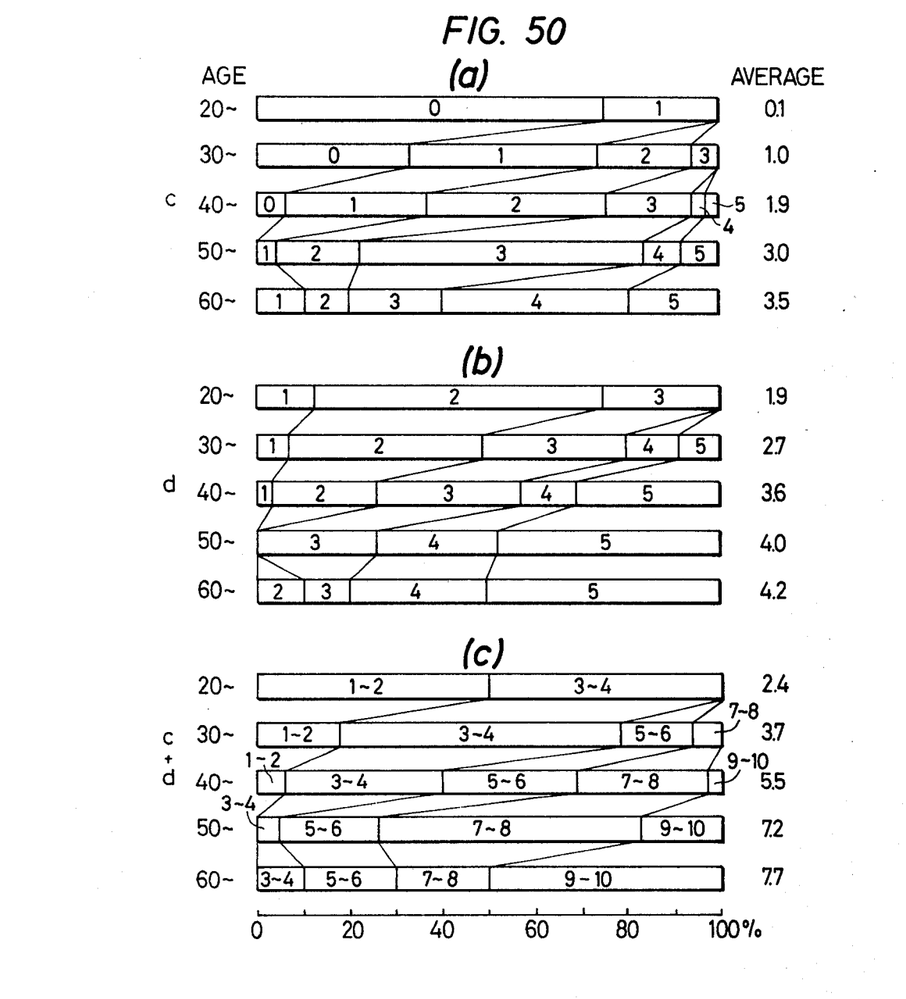
FIG. 50 (a, b and c) is a bar graph showing the distribution of marks by age of an examined group.
Figure 51:
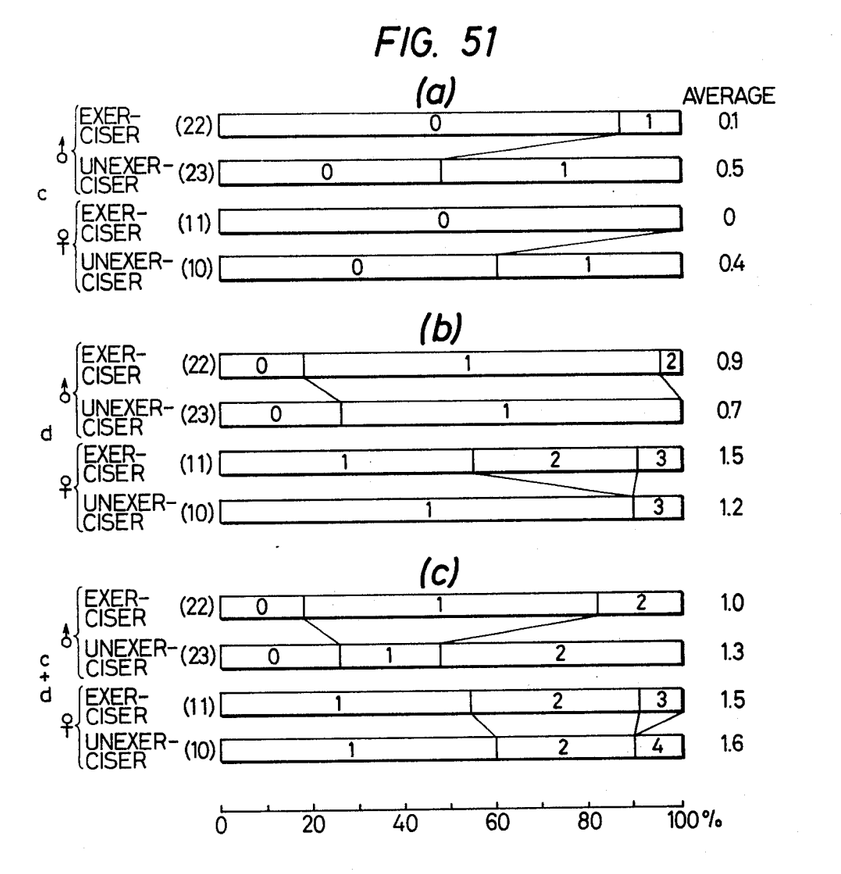
FIG. 51 (a, b and c) is a similar bar graph showing the distribution of marks of a group of male and female exercisers and unexercisers in university students.

The same is true for point D (FIG. 50 (b)). Marks of c+d added together also show a similar tendency (FIG. 50 (c)). It is assumed that those who have obtained higher marks are poor in circulation of the blood in terms of individuals as well as groups. This can be applied to the individuals to represent the quality of blood circulation of a specific individual for use as data for judgement.

Figure 52:
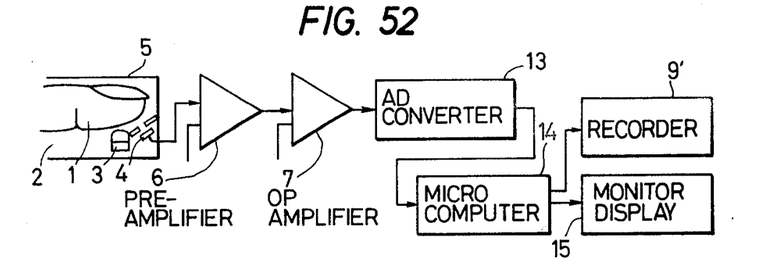
FIGS. 52, 53 and 55 are respectively block diagrams showing modified forms of apparatus.

Further, FIG. 52 (a) (b) (c) are similar distribution views from students in a certain university. The results were that in (c), an excerciser was good whereas in (d), an nonexerciser was good. However, there is a difference between young persons and advanced aged persons, and a difference between individuals. Thus, it is one of advantages of the present invention that the aforesaid difference is clarified and to watch the development thereby to obtain more positive data.

Embodiment 2

In the aforementioned embodiment 1, the CR analog system has been employed in the quadratic differentiated circuit for the characteristic extraction. However, in place of such system, an acceleration plethysmography was manufactured in which as shown in FIG. 52, analog-digital conversion of signals is first carried out by means of an A-D converter 13, after which twice-differentiation is effected in digital terms by means of a microcomputer 14. Then, the clinical diagnosis was carried out with the result that the worsening of the blood flow condition towards arteriosclerosis, myocardial infarction, cerebral apoplexy, subarachnoidal hemorrhage, etc. was quantitatively grasped and accurate diagnosis or presymptoms of these cases became possible. In FIG. 52, reference numeral 9' designates a recorder and 15 designates a monitor display.

Embodiment 3

Figure 53:
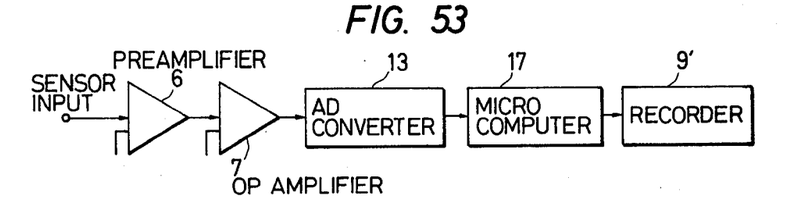
Figure 54:
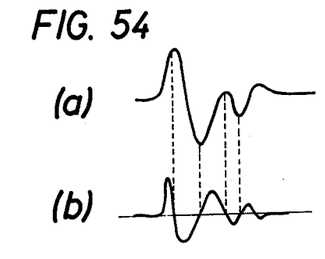
FIG. 54 (a and b) is a comparative view between the quadratic differentiated and cubic differentiated figures.

In the embodiment 1, the distance of the valley B and valley D in the quadratic differentiated figure of the acceleration plethysmograph was obtained from the graph. However, in place of such arrangement, there is proposed a cubic differentiated operation in which as shown in FIG. 53, a microcomputer 17 is used to effect differentiation once again thereby obtaining the position of the valley B, valley D and so on in a numeric manner with the result that an error in reading is reduced to enhance the accuracy of diagnosis by 5%. FIG. 54 (b) is cubic differentiated figure represented on the recorder.

Embodiment 4

Figure 55:
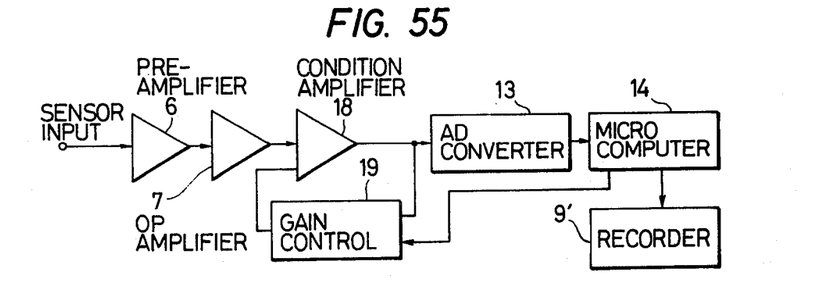

In recording a change of a lapse of time of the content of blood in the blood capillaries, a varying speed thereof, a varying acceleration thereof, etc. on a record paper of the pen-written oscillogram, the dial has been heretofore adjusted by hands to prevent a force-out from the width of record paper or prevent waveforms from being formed into an excessively small size, which operation is cumbersome. Therefore, an automatic gain control circuit 19 was employed as shown in FIG. 55 with the result that recording became possible to be made neatly within a predetermined width to cut examination time by 25%. In FIG. 55, the reference numberal 18 designates a condition amplifier.

Embodiment 5

Only one quadratic differentiated figure of the acceleration plethysmograph has been illustrated in the embodiment 1. However, since the pulse wave is naturally changed somewhat in time intervals by the respiration action, this has to be compensated for. Thus, the embodiments 2 and 3 were further developed so that statistical processes such as arithmetical average of information on the corresponding maximum and minimum values of a plurality of repetitive waveforms are effected to record data. In this manner, the cause of variation due to the respiration action or the like can now be removed satisfactorily.

Embodiment 6

Figure 56:
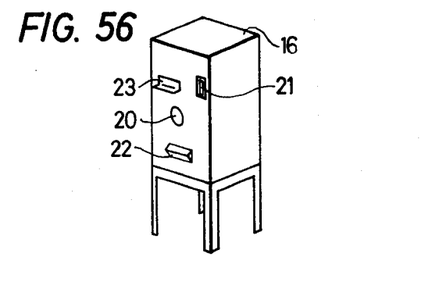
FIG. 56 is a perspective view of a robot doctor to which the present invention is applied.

Since the acceleration pulse wave meter makes possible the prompt provision of simple and accurate diagnostic information, it is possible to install on the street or other public place a robot doctor 16 by which people who conduct themselves in athletic sports such as tennis, jogging or the like can easily receive treatment. To meet said need, an automatic diagnostic apparatus as shown in FIG. 56 was fabricated which comprises a sensor 20 into which a hand's finger-apex is inserted, a coin mechanism 21 which receives change and an ejector 22 which provides a card representative of diagnostic results, the aforementioned diagnostic algorithm being stored into a microcomputer. This apparatus is designed so that when a coin is deposited by a user or when a membership card with a magnetic stripe is inserted into a predetermined location 23, a power source of the apparatus is closed and then, a finger is inserted into the sensor whereby data are obtained to print out the diagnostic result. It was found from an analysis of the case that the apparatus can diagnose in a manner substatially equal to that of the inventor. With this apparatus, a patient need not to take the trouble to go to a hospital and it becomes possible possible to control his own health at a low cost and whenever he wished to do so.

It is noted that the apparatus can give instructions even about a proper amount of exercise, a dietary remedy and the like.

While in the above-described embodiments, the photoelectric type finger-apex pulse wave sensor has been used, pressure type or impedance type can also be used for detection. Further, parts to be detected are not limited to the finger-apex, and the method using the quadratic differentiation and cubic differentiation in accordance with the present invention may be applied to the detection device if the latter can observe a change in the lapse of time of the blood volume contained in the blood capillaries and artery system of an ear-lobe, brain or other parts of the body. Also, in case that a diagnostician is skillful and an inspection record is not necessary, the quadratic differentiated figure merely need be displayed on a Braun tube oscillograph.

As described above, in the present invention, a contrivance has been made to further analyse the conventional pulse wave curve to express it understandably. Yet the use of the present system was made possible to grasp the quality of individual's blood circulation despite the stage in which a minor study has just been made, and it has been apparent that the possibility of a disease may be inferred, and the necessary preventive steps taken.

Moreover, the present invention can advantageously provide high-degree diagnosis and extensive applications not achieved by the conventional plethysmograph, since the result of improvements obtained by training, running, etc. may be judged from the acceleration pulse wave curve, and the apparatus can not only make an early discovery of disease but also observe a transition in the improvement thereof when used as a monitor.

What is claimed is:

1. A plethysmograph comprising a sensor for detecting an increase or decrease in the blood volume of a vascular bed, means producing a pulse waveform signal representative of blood volume, means twice differentiating said pulse waveform signal, means producing an output signal representative of an acceleration pulse wave from said differentiated waveform signal, and means displaying said output signal for analysis of the circulatory system.

2. A plethysmograph according to claim 1, in which said sensor includes a pickup device having an opening adapted to receive a finger, a light source directed at said finger, and a photoelectric element adapted to receive light reflected from said finger.

3. A plethysmograph according to claim 2, in combination with a cabinet containing said plethysmograph and having an opening therein to permit access of the finger to said pickup device, means for actuating said sensor, means converting the final acceleration pulse waveform signals into readable printed form of the diagnostic results, and means responsive to said actuating means for ejecting said printed form from said cabinet.

4. The plethysmograph according to claim 1, in combination with means converting said pulse waveform signals into digital signals, and in which said differentiating means acts upon said converted digital signals.

5. A plethysmograph according to claim 4, in which said display means comprises a pen-writing oscilloscope, in combination with means amplifying the initial pulse waveform signal, and gain control means acting upon said amplifier to control the size of the pen-written display.

6. A plethysmograph according to claims 1 or 4, in combination with means to further differentiate said twice differentiated pulse waveform signal, whereby said output signal is representative of a triple differentiated pulse waveform signal.

* * * * *

UNITED STATES PATENT AND TRADEMARK OFFICE
CERTIFICATE OF CORRECTION

PATENT NO. : 4,432,374
DATED : February 21, 1984
INVENTOR(S) : Hiroshi Osanai

It is certified that error appears in the above-identified patent and that said Letters Patent are hereby corrected as shown below:

On cover page, insert

--[30] Foreign Application Priority Data
Nov. 29, 1980 [JP] Japan ............ 168,396--

Signed and Sealed this

Fourth Day of December 1984

[SEAL]

Attest:

GERALD J. MOSSINGHOFF

Attesting Officer        Commissioner of Patents and Trademarks